United States Patent [19]

Schreier et al.

[11] Patent Number: 5,766,625

[45] Date of Patent: *Jun. 16, 1998

[54] ARTIFICIAL VIRAL ENVELOPES

[75] Inventors: Hans Schreier. Hermitage. Tenn.;
Ramesh Chander. Bombay. India;
Arlene A. Stecenko. Nashville. Tenn.

[73] Assignee: University of Florida Research Foundation, Inc.. San Diego. Calif.

[ * ] Notice: The term of this patent shall not extend beyond the expiration date of Pat. No. 5.753.258.

[21] Appl. No.: 474,814

[22] Filed: Jun. 7, 1995

Related U.S. Application Data

[63] Continuation of Ser. No. 134,156, Oct. 8, 1993, which is a continuation-in-part of Ser. No. 923,016, Jul. 30, 1992, Pat. No. 5,252,348, which is a continuation of Ser. No. 600,641, Oct. 19, 1990, abandoned.

[51] Int. Cl.$^6$ ............................................. A61K 9/127
[52] U.S. Cl. ................... 424/450; 424/192.1; 424/204.1; 424/208.1; 424/812; 264/41; 264/43; 436/829; 935/54
[58] Field of Search ............................. 424/450, 812, 424/192.1, 208.1, 204.1; 264/4.1, 4.3, 4.6; 436/829; 935/54

[56] References Cited

U.S. PATENT DOCUMENTS

| | | | |
|---|---|---|---|
| 4,078,052 | 3/1978 | Papahadjopoulos | 424/450 |
| 4,792,331 | 12/1988 | Philippot et al. | 604/187 |
| 4,927,637 | 5/1990 | Morano et al. | 424/450 |
| 5,059,421 | 10/1991 | Loughrey | 424/417 |
| 5,204,112 | 4/1993 | Hope et al. | 424/450 |
| 5,376,452 | 12/1994 | Hope et al. | 424/450 |

FOREIGN PATENT DOCUMENTS

| | | |
|---|---|---|
| 0032578 | 7/1981 | European Pat. Off. . |
| 0047480 | 3/1982 | European Pat. Off. . |
| 0298280 | 1/1989 | European Pat. Off. . |
| 0306912 | 3/1989 | European Pat. Off. . |
| 2650502 | 5/1978 | Germany . |
| 8805307 | 7/1988 | WIPO . |

OTHER PUBLICATIONS

Weder, H.G., O. Zumbuehl (1984) "The Preparation of Variably Sized Homogenous Liposomes for Laboratory, Clinical, and Industrial Use by Controlled Detergent Dialysis" Liposome Technology 1:79–107.

Deamer, D.W., P.S. Ulster (1983) "Liposome Preparation: Methods and Mechanisms" pp. 27–51.

Weiner, A.L. (1989) "Liposomes as carriers for polypeptides" Advanced Drug Delivery Reviews 3:307–341.

Rigaud, J.-L. et al. (1988) "Mechanisms of Membrane Protein Insertion into Liposomes during Reconstitution Procedures Involving the Use of Detergents. 2. Incorporation of the Light–Driven Proton Pump Bacteriorhodopsin" Detergent–Mediated Reconstitution of Bacteriorhodopsin 27(8):2677–2688.

Grant, C.W. (1986) "Model Membranes Bearing Glycolipids and Glycoproteins" Chemistry and Physics of Lipids 40:285–302.

Rolf Schubert et al. (1991) "Loading of preformed liposomes with high trapping efficiency by detergent–induced formation of transient membrane holes" Chermistry and Physics of Lipids 58:121–129.

McCormick, J.L., R.M. Johnstone (1986) "Asymmetric Reconstitution of the Glucose Transporter from Ehrlich Ascites Cell Plasma Membrane: Role of Alkali Cations" Archives of Biochemistry and Biophysics 248(1):379–389.

Helmke, S.M., B.D. Howard (1987) "Fractionation and Reconstitution of the Sarcoplasmic Reticulum $Ca^{2+}$ Pump Solubilized and Stabilized by CHAPS/Lipid Micelles" Membrane Biochemistry 7:1–22.

Gaymard, F. et al. (1993) "A test for screening monoclonal antibodies to membrane proteins based on their ability to inhibit protein reconstitution into vesicles" Biochimica et Biophysica Acta. 1150:73–78.

Scheule, R.K. (1986) "Novel Preparation of Functional Sindbis Virosomes" Biochemistry 25:4223–4232.

Cornell, R.B. (1991) "Regulation of CTP:Phosphocholine Cytidylyltransferase by Lipids. 2. Surface Curvature, Acyl Chain Length, and Lipid–Phase Dependence for Activation" Biochemistry 30:5881–5888.

Richard, P. et al. (1990) "Reconstitution of $CF_0F_1$ into liposomes using a new reconstitution procedure" Eur. J. Biochem. 193:921–925.

Perrin, P. et al. (1985) "Rabies immunosome (subunit vaccine) structure and immunogenicity. Pre–and post–exposure protection studies" Vaccine 3:325–332.

Laurence, J. (1990) "Review Novel Vaccination and Anti-receptor Strategies Against HIV" Aids Research and Human Retroviruses 6(2):175–181.

Ho, R.J.Y., R.L. Burke, T.C. Merigan (1989) "Antigen–Presenting Liposomes Are Effective in Treatment of Recurrent Herpes Simplex Virus Genitalis in Guinea Pigs" Journal of Virology 63(7):2951–2958.

El Guink, R.M. Kris, G. Goodman–Snitkoff, P.A. Small, Jr., R.J. Mannino (1989) "Intranasal immunization with proteoliposomes protects against influenza" Vaccine 7:147–151.

Gould–Fogerite, Susan, et al. (1988) "The Reconstitution of Biologically Active Glycoproteins into Large Liposomes: Use as a Delivery Vehicle to Animal Cells" Advances in Membrane Biochemistry and Bioenergetics 569–586.

(List continued on next page.)

Primary Examiner—Gollamudi S. Kishore
Attorney, Agent, or Firm—Saliwanchik, Lloyd & Saliwanchik

[57] ABSTRACT

The production of artificial viral envelopes by a novel double-detergent dialysis technique is disclosed. Specifically exemplified is the production of HIV-1 and RSV viral envelopes. The resulting artificial viral envelopes are essentially identical to the natural virus with regard to characteristics which are relevant to immunogenicity and intracellular transfer of encapsulated material.

28 Claims, No Drawings

OTHER PUBLICATIONS

Nussbaum, O., et al. (1987) "Reconstitution of Functional Influenza Virus Envelopes and Fusion with Membranes and Liposomes Lacking Virus Receptors" J. Virol. 61(7):2245–2252.

Haddad, R.S., L.M. Hutt–Fletcher (1989) "Depletion of Glycoprotein gp85 from Virosomes Made with Epstein Barr Virus Proteins Abolishes Their Ability To Fuse with Virus Receptor–Bearing Cells" J. Virol. 63:4998–5005.

Oth, D., et al. (1987) "The Association of the Rabies Glycoprotein with Liposome (Immunosome) Induces an in Vitro Specific Release of Interleukin 2" Cell. Immunol. 108:220–226.

Thibodeau, Lise, M. Chagnon, L. Flamand, D. Oth, L. Lachapelle, C. Tremblay, L. Montagnier. (1989) C.R. Acad. Sci. Paris 309(III):741–747.

Anderson, W. French (1992) "Human Gene Therapy" Science 256:808–813.

Riordan, Michael L., John C. Martin (1991) "Oligonucleotide–based therapeutics" Nature 350(6317):442–443.

Hug, Peter, Richard G. Sleight (1991) "Liposomes for the transformation of eukaryotic cells" Biochim. Biophys. Acta 1097:1–17.

Brigham, Kenneth L., Hans Schreier (1993) "Cationic Liposomes and DNA Delivery" Journal of Liposome Research 3(1):31–49.

Senior, J.H., et al. (1991) "Interaction of positively–charged liposomes with blood: implications for their application in vivo" Biochim. Biophys. Acta 1070:173–179.

Deamer, D.W., P.S. Uster (1983) "Liposome Preparation: Methods and Mechanisms" pp. 27–51.

ARTIFICIAL VIRAL ENVELOPES

This is a continuation of application Ser. No. 08/134,156, filed Oct. 8, 1993, now pending which is a continuation-in-part of co-pending application Ser. No. 07/923,016, filed Jul. 30, 1992, now U.S. Pat. No. 5,252,348, which is a continuation of application Ser. No. 07/600,641, filed Oct. 19, 1990, now abandoned.

BACKGROUND OF THE INVENTION

Enormous efforts are currently being made to develop a vaccine against HIV-1 (Laurence, J. [1990] AIDS Res. 6:175–181). Currently tested systems employ either killed virus, stripped of its coat, or one of the HIV proteins, either surface glycoproteins (gp120, gp160) or core proteins (p24, hgp30). The main limitation with subunit protein vaccines is their poor immunogenicity, even if combined with an adjuvant, e.g., muramyltripeptide or others.

Another approach, used by several investigators, has been to enhance the immunogenic activity of subunit vaccines by preparing protein-containing lipid vesicles, called "proteoliposomes," "immunoliposomes," "immunosomes," "virosomes," or the like. Methods to prepare these vesicles vary widely, however, they are based on one of the following protocols: proteins are usually (i) passively bound to lipids by van der Waal's or hydrophobic interaction; (ii) covalently bound to lipids, or to phospholipid molecules (mainly phosphatidylethanolamine), via divalent coupling agents such as SPDP and others; or (iii) reconstituted with extracted viral lipids, phospholipids, or a combination of both, from detergent-solubilized lipid-protein mixtures.

Only a small number of investigators (Ho, R. J. Y., R. L. Burke, T. C. Merigan [1989] J. Virology 63:2951–2958; El Guink, N., R. M. Kris, G. Goodman-Snitkoff, P. A. Small Jr., R. J. Mannino [1989] Vaccine 7:147–151; Gould-Fogerite, S., J. E. Mazurkiewicz, D. Bhisitkul, R. J. Mannino [1988] In Advances in Membrane Biochemistry and Bioenergetics [C. H. Kim et al., eds.] Plenum Press, New York, pp. 569–586; Nussbaum, O., M. Lapidot, A. Loyter [1987] J. Virol. 61:2245–2252; Haddad, R. S., L. M. Hutt-Fletcher [1989] J. Virol. 63:4998–5005; Oth, D., G. Mercier, P. Perrin, M. L. Joffret, P. Sureau, L. Thibodeau [1987] Cell Immunol. 108:220–226; Thibodeau, L., M. Chagnon, L. Flamand, D. Oth, L. Lachapelle, C. Tremblay, L. Montagnier [1989] CR Acad. Sci. Paris 309(III):741–747) made an effort to insert proteins so that binding and/or immunogenicity was retained upon reconstitution of the mixture, usually via detergent dialysis. However, in most cases, arbitrary phospholipid mixtures are used which do not represent the accurate lipid composition of the viral envelope. Only El Guink et al. (1989, supra) used control liposomes (without viral proteins) similar to the natural viral lipid composition.

Thibodeau et al (1989, supra) describe a method of "anchoring" HIV gp160 on the surface of liposomes to prepare "HIV-immunosomes." However, the liposome composition is not disclosed, and the "anchoring" is achieved by simple incubation of preformed liposomes with the purified gp160.

In contrast to Thibodeau et al.'s (1989, supra) approach, we have generated a viral envelope identical to the HIV-1 envelope with respect to its lipid composition, an approximately equimolar lipid:cholesterol ratio, unilamellarity, and vesicular size. Furthermore, the incorporation of gp160 was achieved by partial re-solubilization of the lipid envelopes in order to maintain the correct three-dimensional protein conformation by incorporation of the hydrophobic gp41 part of gp160 into the lipid envelope. Using our innovative approach, it is now possible to formulate subunit vaccines which are superior to conventional vaccines.

The subject invention, which utilizes a unique double-detergent dialysis procedure, results in a viral envelope with proteins only on the surface, as they should be, rather than randomly intermingled with the envelope lipid portion.

The subject invention further pertains to materials and methods for gene therapy (Anderson, W. F. [1992] Science 256:808–813) and oligonucleotide therapy (Riordan, M. L., J. C. Martin [1991] Nature 350:442–443). These new procedures are emerging as clinically viable therapeutic regimens for genetic, neoplastic, and infectious diseases. The general basis for these therapies is the insertion of DNA into the cells of an animal which has defective DNA or could otherwise benefit from the expression of new DNA or the prevention of expression of the current DNA One of the major obstacles which has, to date, limited the usefulness of these procedures pertains to the difficultly in selectively and efficiently delivering DNA to the desired cells and having that DNA transported to the desired cells. Approaches which have previously been used include insertion of human genes in viral vectors including recombinant retrovirus, adenovirus, adeno-associate virus, and herpes simplex virus-1. Also, recombinant bacterial plasmids have been used. Viral vectors transfect cells directly, whereas plasmid DNA can be delivered with the help of cationic liposomes (lipofection), polylysine conjugates, gramicidin S, or combinations thereof.

Major areas of application of gene therapy include replacement of the cystic fibrosis transmembrane regulator gene and the $\alpha_1$-antitrypsin gene, arrest of human immunodeficiency virus infection, reversal of tumorigenicity, and cancer immunization. Oligonucleotide therapy is principally focusing on the same areas, although the approach is to halt DNA transcription or messenger RNA translation with code-blocking triple helix-forming, or "antisense," oligomers.

Liposomes in many forms have been investigated as potential gene or antisense carrier systems. pH-sensitive liposomes, cationic liposomes, and virosomes have been investigated in this regard (reviewed by Hug, P., R. G. Sleight [1991] Biochim. Biophys. Acta 1097:1–17). Only cationic liposomes have been employed successfully in vitro and in vivo (reviewed by Brigham, K. L., H. Schreier [1993] J. Liposome Res. 3:31–49), serious doubts remain as to their potential in vivo toxicity (Senior, J. H., K. R. Trimble, R. Maskiewicz [1991] Biochim. Biophys. Acta 1070:173–179).

We have generated viral envelopes which interact selectively with cell surface receptors and deliver, similar to the discharge of natural virus DNA or RNA into human cells, their encapsulated material, including DNA plasmids, to the interior of cells.

BRIEF SUMMARY OF THE INVENTION

Disclosed are novel artificial viral envelopes, essentially identical to natural viral envelopes, e.g., to the human immunodeficiency virus (HIV-1), the respiratory syncytial virus (RSV), or other viruses, and a novel method, double-detergent dialysis, essential to prepare same.

Natural viral envelopes are unique in their cholesterol:phospholipid ratio of about 0.8–1.2 and, until now, could not be reproduced by any known preparation technique.

The subject invention describes a novel method, double-detergent dialysis, which can be used to prepare lipid vesicles in general and viral envelopes in particular. The first step of the novel process is the preparation of lipid vesicles without glycoprotein from a detergent-solubilized lipid mixture at a unique lipid:detergent ratio. Next, glycoproteins are inserted into the preformed vesicles by partial micellation with another detergent followed by dialysis. The process has been adapted to reproducibly yield both small (<5 ml) laboratory scale samples as well as sterile large batches (>100 ml). An important aspect of this method is that the two steps are independent processes. Thus, a large reservoir of concentrated lipid envelopes can be prepared and stored while individual batch sizes of the final envelope containing the surface protein, or the desired composite epitopes of surface proteins, can be prepared upon demand.

The artificial viral envelopes can be characterized by: (i) an advantageous phospholipid:cholesterol ratio of about 1:1; (ii) a virus-specific phospholipid composition; (iii) a homogenous size distribution around 250 nm, similar to natural viral size; (iv) a uniquely stable, rigid, unilamellar structure; (v) envelope glycoproteins such as the HIV-1 gp160, RSV G (aggregation) and F (fusion) proteins, and others, inserted in the outer surface; (vi) high fusogenic activity; (vii) specific binding to their monoclonal antibodies confirming the intact conformation of the surface glycoproteins; and (viii) selective binding to cell surface receptors such as the CD4 receptor on human T-cells.

The following applications of the artificial viral envelopes are proposed: (i) synthetic subunit vaccines; (ii) highly targetable and fusogenic drug delivery devices for delivery of antiviral agents to infected cells; (iii) highly targetable and fusogenic drug delivery devices for delivery of highly specific cell destructing agents; (iv) highly efficient transfection device for the introduction of genetic materials, including DNA, plasmids, and oligodeoxynucleotides, into animal, bacterial, and plant cells; (v) highly efficient device for the intracellular delivery of macromolecules including peptides and proteins; and (vi) non-biohazard in vitro model systems for viral infectivity.

DETAILED DESCRIPTION OF THE INVENTION

The artificial lipid vesicles of the subject invention are characterized by: (i) a cholesterol:phospholipid ratio of about 0.8 to about 1.2, similar to that of natural viral envelopes; (ii) a phospholipid composition similar to the natural phospholipid mixture of viral envelopes; (iii) a homogenous size distribution in the range of about 50 to about 500 nm, which is similar to that of the natural viral particle; and (iv) a physically stable unilamellar membrane structure. In one preferred embodiment of the invention, the novel lipid vesicles may be further characterized by (v) envelope proteins such as the HIV-1 gp160, RSV G (aggregation) and F (fusion) proteins, and others, inserted in the outer surface; (vi) high fusogenic activity; (vii) specific binding to their monoclonal antibodies confirming the intact conformation of the surface proteins following insertion; and (viii) selective binding to cell surface receptors such as the CD4 receptor on human T-cells.

Preferably, the phospholipid composition of the synthetic viral envelopes should be similar to the natural viral composition and should comprise phosphatidylcholine (PC), phosphatidylserine (PS), phosphatidylethanolamine (PE), and sphingomyelin (SM). The envelope may further comprise additional lipids such as phosphatidylinositol.

The artificial lipid vesicles are prepared by a novel method—double detergent dialysis. As specifically exemplified herein, this method consists essentially of two steps: (1) preparation of the phospholipid/cholesterol envelope by solubilization of the lipids and cholesterol with sodium cholate or other appropriate detergent as the solubilizing agent at a unique molar ratio of approximately 45 1, followed by removal of the detergent by exhaustive dialysis against phosphate-buffered saline (PBS); and (ii) insertion of protein(s) in the outer surface of the preformed vesicles by partial micellation with sodium deoxycholate or other appropriate detergent at an approximate ratio of 8:1 and removal of the detergent by exhaustive dialysis as before in step (i). As would be appreciated by a person skilled in this art the term "partial micellation" refers to a vesicle membrane which is "softened" to the point that the vesicle flattens out and acquires a disc- or dumb-bell-like shape which reverses into a vesicular structure upon removal of the detergent; however, the vesicles are not solubilized (micellized) to the point that they lose their intrinsic bilayer structure and become true mixed micelles again. This process can be controlled by monitoring the scattering of light of the vesicles using a laser light scattering instrument. Enough detergent is introduced into the vesicle dispersion to maintain the light scattering signal. Loss of the light scatter signal indicates true solubilization, thus excess of detergent and loss of the vesicular structure in favor of a micellar structure. In the specific system exemplified herein, the preferred molar ratio of detergent:lipid that maintains the partially micellated disc-like vesicular structure was found to be about 8:1.

The method of the subject invention can be readily modified by a person skilled in the art to use, for example, other soloblizing agents or buffers. Generally, the proteins which are inserted into the preformed vesicles will be glycoproteins but other proteins can be used, so long as they remain inserted in the lipid vesicle.

In the first step of the subject invention, the detergent:lipid ratio can be from about 30:1 to about 60:1 and is preferably from about 40:1 to about 50:1 and is most preferably approximately 45:1. Although the skilled artisan may be able to manipulate the procedures described herein to utilize detergent ratios over the broad ranges given above, it should be noted that relatively small changes in these ratios can have significant effects. Therefore, use of detergent to lipid ratios in the 40:1 to 50:1 range is preferred. For the second dialysis step, the detergent:lipid ratio can be from about 5:1 to about 10:1 and is most preferably about 8:1. Useful detergents are well known to those skilled in the art and include, but are not limited to, bile salts (sodium cholate, deoxycholate, taurocholate, etc.), CHAPSO, octylglucoside, TRITON-X derivatives, etc. These detergents can be anionic such as CHAPSO, or nonionic such as octylglucoside or Triton-X. The selection of the detergent is determined taking into account the compatibility of a particular detergent with the surface protein to be inserted.

Dialysis and related methodologies can be carried out using any of a number of techniques which are known to those skilled in the art. For example, bag, disc, flow-through, and counter-flow dialysis techniques and apparatus may be utilized. A wide range of lipid:protein molar ratios can be used. This range may be, for example, from about $1\times10^6$:1 or higher to around 100:1 or lower. The ultrastructure should preferably be unilamellar, however, oligolamellar may also be acceptable for some purposes.

An important aspect of the double-detergent dialysis method is that the two steps are independent processes. During the first step, unilamellar lipid envelopes in a size range of about 50 to about 500 nm or, preferably, about 150 to about 350 nm or, most preferably, approximately 250 nm, essentially identical to natural viral membranes, are generated. These preformed envelopes are of superior physical stability with an average size, and size distribution, that remain essentially unchanged over several months when stored under refrigeration.

The envelopes produced according to the subject invention can be freeze-dried and thus preserved for extended periods of time. The freeze-drying, or other means of preservation, can be done either before or after insertion of the protein onto the envelope. The use of freeze-drying procedures can reduce or eliminate the need for keeping vaccines refrigerated and, therefore, can be very important for field uses, especially in underdeveloped countries. The stability of the lipid vesicles can be improved even further by polymerization of one or more of the phospholipid components.

Thus, a large reservoir of concentrated lipid envelopes can be prepared and stored while individual batch sizes of the final artificial viral envelope containing the surface protein or their desired composite epitopes can be prepared upon demand. The method is flexible so that batch sizes in a range of less than 5 ml to liter quantities can be prepared reproducibly and under sterile conditions using, for example, either teflon dialysis cells or flow-through hollow fiber dialysis apparatus.

An important feature of the viral envelopes produced according to the subject invention is that the protein, in the preferred embodiment, is inserted only on the outside surface of the envelope. Whole proteins or antigenic determinants or epitopes may be used on the lipid vesicle. As used herein the terms "epitopes" and "determinants" are used interchangeably to refer to portions of proteins or peptides which either raise an immune response or are recognized by or react with components of the immune system. Advantageously, this protein is exposed and available for antigenic and immunologic reactivity. The protein which is applied to the envelope may be natural protein isolated from any viral, bacterial, or other source. Also, the protein may be produced through recombinant means. The recombinant protein may be, for example, reactive epitopes from a virus of interest. Also, the protein applied to the envelope may be a cocktail of proteins or epitopes from a single virus (or other entity) or from several viruses (or other entities). The novel envelopes can be actively targeted to specific cells via receptor recognition, e.g., CD4 receptor; at the same time, they are naturally targeted to macrophages which in many cases are reservoirs for viral and bacterial diseases. In addition, viral core proteins may be entrapped within the artificial envelopes which may further enhance their immunogenic response.

According to the subject invention, the lipid envelopes produced according to the unique process can be coated with proteins from any one of a number of viruses, bacteria, and parasites. Specifically exemplified herein is the construction of artificial RSV and HIV-1 envelopes. The following applications of an artificial HIV-1 viral envelope can be envisioned:

1. Artificial HIV-1 envelopes, being identical to the natural HIV-1 envelopes in size and chemical composition, would induce both a humoral and cellular immune response; thus, they may serve as a synthetic subunit vaccine against HIV-1. Several significant advantages of such a synthetic vaccine over vaccination with a natural modified HIV preparation can immediately be appreciated: (a) since the artificial HIV-1 envelope is void of genetic information, there is no danger of infection; (b) the synthetic vaccine is likely to be more immunogenic due to proper presentation of the antigen to, lymphocytes; (c) insertion of desired composite epitopes will yield highly efficacious vaccines; and (d) antigenic drift, once identified and reproduced by recombinant techniques, can immediately be simulated with the synthetic vaccine.

2. Due to the unique capability of the HIV-1 virus to bind to and fuse with $CD4^+$ cells, the artificial HIV-1 envelope may be utilized as a novel "target-seeking" drug delivery system for antiviral drugs for delivery of antiviral agents specifically to HIV-1 infected cells. This is an important and novel aspect of the artificial HIV-1 envelope since both the antiviral killing efficacy of antiviral drugs and stimulation of production of virus-neutralizing antibodies can be combined in the same delivery device in order to effectively protect an infected individual from spreading of the infection and provide a potential cure of the disease.

3. Following the same rationale as in 2., due to the unique capacity of the HIV-virus to gain entry into $CD4^+$ cells and discharge its genetic information into those cells, the artificial HIV-1 envelope may be utilized as a novel gene (or other gene-related constructs such as oligonucleotides) delivery system.

4. The investigation of biochemical and immunological pathways as well as the development of vaccines and antiviral drugs is complicated by restrictive regulations necessary to protect personnel from inadvertent exposure to HIV-1. Since the artificial HIV-1 envelope does not contain genetic information, its use would be much less restricted. Therefore, the artificial HIV-1 envelope can serve (a) as an in vitro model for viral infectivity, particularly to investigate viral cell binding and cell fusion, and (b) as an in vitro efficacy screening test of antiviral drugs that act on the principle of viral membrane perturbation or specific binding to viral surface proteins.

Artificial RSV envelopes can serve as a synthetic vaccine against RSV in a similar fashion as described above for HIV-1. In addition, it can serve as a drug delivery system for antiviral agents such as ribavirin and others for the treatment of pulmonary RSV infections. Artificial RSV envelopes are highly fusogenic and, therefore, may be used as an efficient fusogenic intracellular drug carrier, specifically for the aerosol delivery of antiviral drugs to infection sites in lung epithelial cells.

A virtually unlimited number of artificial viral envelopes can be prepared and applied as described for the examples above using recombinant or isolated surface determinants. For example, the novel lipid vesicles of the subject invention can be used in connection with a number of human viruses including arboviruses including alphaviridae (Easter, Western, and Venezuelan equine encephalitis virus), flaviviridae (St. Louis encephalitis virus), bunyaviridae (California encephalitis virus), orbivirus (Colorado tick fever), yellow fever virus, Dengue and Dengue hemorrhagic fever virus, Japanese encephalitis virus, Murray Valley encephalitis virus, Chikungunya virus, tick-borne encephalitis virus, Kyasanur Forest virus, Crimean hemorrhagic fever and Congo virus, Rift Valley Fever virus; arenaviruses including lymphocytic choriomeningitis virus, Argentinean and Bolivian hemorrhagic fever virus, and Lassa fever virus; coronaviruses including infectious bronchitis virus; human cytomegalovirus; enteroviruses including polioviruses, Coxsackieviruses A and B, echoviruses, and hepatitis A virus; Epstein-Barr virus; gastroenteritis-causing viruses including Norwalk group of viruses and rotaviruses; bunyaviruses including hantaviruses (hemorrhagic fever with renal syndrome); hepatitis viruses including A, B, delta, non-A-non-B; herpes simplex viruses 1 and 2; varicella zoster virus (human herpes virus 3); influenza virus (A,B,C); paramyxoviruses including parainfluenza virus type 1–3; respiratory syncytial virus; measles virus; mumps virus; rabies and rabies-related viruses; retroviruses including human T-lymphotrophic virus type I and II (HTLV-VII) and human immunodeficiency virus type 1 and 2 (HIV-1/2); rhinoviruses; rubella virus; orthopoxvirus group including smallpox virus; B19 parvovirus; human papilloma viruses; Newcastle disease virus; Senilild Forest virus; encephalomyocarditis virus; Marburg and Ebola virus (African hemorrhagic fever); vesicular stomatitis virus; DNA viruses including adenoviruses (41 types) (Acute Respiratory Disease ARD); natural, complete, truncated or synthetic viral glycoproteins and chimeras thereof, viral proteins and peptides used to prime MHC class-I-restricted and class-II-restricted cytotoxic T lymphocytes (CILs); viral protein fragments (e.g., from RSV G glycoprotein) which induce T helper and B cells and chimeras thereof.

This technology can also be used with animal viruses such as bovine viral diarrhea virus, hog cholera virus, border disease virus (sheep); infectious bursal disease virus (chicken), Sindbis virus (equine encephalitis); canine distemper virus, phocid distemper virus, rinderpest virus, peste des petits ruminants virus, foot-and-mouth disease virus, feline immunodeficiency virus, imrnian immunodeficiency virus, bovine leukemia virus.

Epitopes from bacterial and parasitic disease agents such as *Corynebactenum diphtheriae* (diphtheria), *Clostridium tetani* (tetanus), *Neissefia meningitidis* (meningitis), *Streptococcus pneumoniae* (pneumonia), *Haemophilis influenzae* (meningitis) (capsular polysaccharides), *Bordatella pertussis* (whooping cough) (pertussis toxin), *Salmonella typhi* (typhoid fever), *Vibiio cholerae, Coxiella bumetii* (Q fever), *Mycobactenium tuberculosis*, atypical mycobacteria including *M. avium-intracellulare* and *M. kansasii*, Shigella, leishmaniasis, schistosomiasis, *Plasmodium falciparum* (malaria), Eimefia (coccidiosis) (poultry) can also be used with the novel envelopes.

The novel lipid vesicles of the subject invention can also be used to transfer genetic material to bacterial cells, yeasts, animal (including human) cells, or plant cells. The excellent and surprising fusogenic properties of the vesicles of the subject invention make these vesicles excellent for delivering a variety of molecules and substances to specific cells. The material which is delivered can include genetic material such as isolated DNA; synthetic, PCR, or cloned DNA; plasmids; RNA; triple helix-forming oligodeoxynucleotides; and anti-sense nucleotides. The genetic material may be incorporated into the lipid vesicle during the first step of the novel process such that the genetic material is encapsulated within the lipid vesicle. Artificial lipid vesicles could be used in plants as vectors carrying t-DNA for the transfer of host-defense response genes; or to create, host "resistance" genes, e.g., import *Bacillus thuningiensis* crystal-protein gene to express *B. thuringiensis* toxin as "bioinsecticide;" or to deliver anti-sense nucleic acid, e.g., anti-sense construct of polygalacturonase in tomato plants; or to deliver viral satellite RNA; or to deliver ribozymes to induce autocatalytic RNA cleavage, e.g., of the satellite tobacco ringspot virus RNo Viral envelopes may be from the groups of reoviruses, robemoviruses, tymoviruses, tombusviruses, inteoviruses, tobraviruses, furoviruses, comoviruses, nepoviruses, hordeiviruses, cucomoviruses, ilarvirusec, bromoviruses, alfalfa mosaic virus, rice stripe virus, tomato spotted wilt virus, velvet tobacco mottle viruses.

In addition to their uses as subunit vaccines and vectors, the envelopes described herein can be used in a variety of therapeutic applications including the destruction of viruses or specific cells such as cancer cells. Also, these envelopes can be appropriately modified to play a role in the modulation of biological pathways or reactions, especially in the endocrine and immune systems. These envelopes can be targeted to T-cell lymphocytes and their subpopulations. Advantageously, receptorspecific drug/toxin modulator delivery systems can be tailored to any receptor that recognizes peptide or protein moieties that can be inserted in the viral envelope. The encapsulated material delivered by the liposomes of the subject invention can be immunomodulatory. Immunosuppressants such as cyclosporin A can be effectively delivered as can immune enhancers such as interleukin-1, or other interleukin molecules, an interferon, or muramil dipeptide or tripeptide. In this embodiment, the fusogenic liposome binds with a cell and its encapsulated material becomes inserted into the cell. In this embodiment, it is not essential for proteins to be inserted into the surface of a liposome; however, it will often be highly desirable to have these surface proteins (or other molecules) to direct the liposomes to a specific location or cell type.

Furthermore, the envelopes described herein can be advantageously employed to transfect cells with transgenes either for gene markcing, replacement of a missing gene, or insertion of a therapeutic gene. Examples include transfection of pulmonary endothelial or epithelial cells with a missing cystic fibrosis transmembrane regulator (CFTR) gene or the human $\alpha_1$-antitrypsin gene, or other genes in other areas of the body including diseased areas such as neoplastic, fibrotic, or degenerated tissue.

The use of the lipid vesicles of the subject invention to deliver drugs, toxins, or other substances can be accomplished in at least two ways. First, the lipid vesicle may be constructed to encapsulate the drug or toxin of interest. The vesicle could then be coated with a protein determinant which directs the lipid vesicle (and encapsulated substance) to the desired location. Alternatively, the lipid vesicle may be conjugated to any number of moieties. For example, the lipid vesicle may be conjugated to a toxin by coating the vesicle with glycoproteins which act as spacer arms to connect the lipid vesicle to the toxin. These glycoproteins which are embedded in the lipid vesicle may have, for example, a cysteine residue at the free end of the protein which would facilitate conjugation to a toxin via a disulfide bond.

The technology described herein can be used to treat various diseases including, but not limited to, T-cell malignancies related to retrovirus activity such as acute lymphoblastic leukemia, Kawasaki's disease, HIodgkin's disease; sarcoidosis; neurological syndromes including multiple sclerosis and chronic neurological diseases including subacute sclerosing panencephalitis, progressive multifocal leukoencephalopathy, Kuru and Creutzfeldt-Jakob disease; autoimmune diseases including degenerative joint disease. Cancers with known viral agents include cervical cancer (herpes simplex virus 2, human papilloma virus); Burkitt lymphoma (Epstein-Barr virus); nasopharyngeal carcinoma (Epstein-Barr virus); hepatocellular carcinoma (hepatitis B virus).

The drugs and other active agents that these envelopes can be used with include antiviral, antibiotic, and antifungal drugs. Also, the envelopes can be linked to toxins, polynucleotides, immunomodulators, and membrane-perturbing agents.

Further embodiments for practicing the subject invention include the use of "marker genes" to monitor the state of disease, and the duration of the modified cells in the diseased tissue, e.g., in order to follow the in vivo fate of tumor infiltrating lymphocytes (TILs) or transplanted hepatocytes in the liver. Alternatively, the subject invention can be used in the replacement of a defective or missing gene in a human cell to correct its malfunction, e.g., replacement of the mutant cystic fibrosis transmembrane conductance regulator (CFTR) gene, human $\alpha_1$-antitrypsin, $\beta$-glucocerebrosidase (Gaucher's disease), and adenosine deaminase (ADA) deficiency.

The compositions of the subject invention can be delivered to humans or animals by a number of methods known to those skilled in the art. For example, the lipid vesicles may be formulated for parenteral, oral, or topical administration. Also, in a preferred embodiment of the invention, the compounds may be administered as an aerosol spray or as nasal or ocular drops. The formulations will typically be in a saline/buffer solution. The liposomes of the subject invention can also be prepared as an aerosol powder, particularly for pulmonary use.

Materials Used

Phospholipids were purchased from the following sources: egg phosphatidylcholine (PC) (lot #37F-8420), phosphatidylserine (PS) (lot #99F-83561) from bovine brain, egg phosphatidylethanolamine (PE) (lot #58F-8371), cholesterol from porcine liver (lot #36F-7040), deoxycholic acid (lot #108F-0331) and sodium cholate (lot #78F-0533) were from Sigma Chemical Co., St. Louis, Mo. Egg sphingomyelin (SM) (lot #ESM-22) was from Avanti Polar Lipids, Pelham, Ala. The composition of phosphate buffered saline (PBS) was NaCl 137 mM, KCl 2.7 mM, $Na_2HPO_4$ 8.1 mM, $KH_2PO_4$ 1.5 mM, with 0.5 mM sodium azide (lot #13F-0600) (Sigma). Spectra/Por 2 (mol. cut-off 12–14,000) membrane discs were used for dialysis in teflon dialysis cells.

HIV-1 gp160 envelope protein (lot #8962R-1) at a concentration of 100 µ/ml in 5 mM Tris buffer containing 0.005% polysorbate 20 was from MicroGeneSys, Inc., West Haven, Conn. According to the manufacturer's specifications, it is a full-length glycosylated recombinant protein derived from the env gene of HIV-1. The protein is produced in insect cells using the baculovirus expression system and purified by low pressure, low temperature chromatography.

RSV glycoproteins F and G were obtained from Dr. E. Walsh, Rochester, N.Y., and were purified by afnity chromatography according to published methods. Purity was assessed by SDS polyacrylamide gel electrophoresis and Coomassie Blue stain. Western blots showed no cross-reactivity of F glycoprotein with G glycoprotein and vice versa.

HEp-2 cells were grown on sterile coverslip flasks at 37° C. and 5% $CO_2$. When the cells were approximately 50% confluent, they were washed with PBS and then used to perform fusion experiments.

The following examples illustrate and exemplify the objectives and embodiments of the present invention. However, the invention is in no way restricted to the examples presented.

EXAMPLE 1

Preparation of Artificial HIV-1 or RSV Envelopes (Without Protein)

Stock lipid solutions were prepared as shown in Table 1. Briefly, enough cholesterol or phospholipids were dissolved individually in 10 ml chloroform to give the concentrations indicated in Table 1. Sodium cholate stock solution was prepared in methanol.

TABLE 1

Lipid Composition and Stock Solutions

| | mg/10 ml $HCCl_3$ | MW | µ moles/ 10 ml | mole % of total PL |
|---|---|---|---|---|
| cholesterol (CH) | 38 | 386 | 98.4 | |
| phosphatidylcholine (PC) | 20 | 786 | 25.4 | 23.7 |
| phosphatidylethanolamine (PE) | 18 | 743 | 24.2 | 22.6 |
| phosphatidylserine (PS) | 23 | 832 | 27.6 | 25.7 |
| sphingomyelin (SM) | 22 | 731 | 30.1 | 28.1 |
| TOTAL PHOSPHOLIPID (PL) | 83 | | 107.3 | 100.0 |
| TOTAL LIPID (incl. CH) | 121 | | 205.7 | |
| Sodium cholate | 2000[1] | 430.6 | 4644.7 | |

[1]in methanol

As shown in Table 2, the ratio of total phospholipid:cholesterol was approximately 1. The detergent:total lipid ratio was 9289.4 µMole/10 ml to 205.7 µMole/10 ml, or approximately 45:1.

TABLE 2

Lipid:Cholesterol and Lipid:Detergent Ratio

| | CONC. (µMOLE/10 ml) | | |
|---|---|---|---|
| | Total Phospholipid | Cholesterol | Molar Ratio |
| Initial | 107.3 | 98.4 | 0.92 |
| Recovered after Dialysis | 79.4 (74.0%) | 69.2 (70.3%) | 0.87 |

[1]Total amount of detergent used: 4 mg (20 µl) = 9289.4 µmoles

The phospholipid composition of artificial and natural HIV-1 envelopes (Gordon, L. M., F. C. Jensen, C. C. Curtain, P. W. Mobley, R. C. Aloia (1988) In *Lipid Domains and the Relationship to Membrane Function* [R. C. Aloia et al., eds.] Alan R. Liss, Inc., New York, pp. 255–294) is shown in Table 3. The minor fractions of 2.1 mole % phosphatidylinositol and 0.9 mole % phosphatidic acid, and the 5 mole % of "other" lipids (Gordon et al. supra) were substituted by a larger fraction (25.7 mole % vs. 15.1 mole % in the natural membrane of PS.

TABLE 3

Lipid Composition of Artificial and Natural HIV-1 Envelope

| | MOLE % of Total Phospholipids | | | | | | |
|---|---|---|---|---|---|---|---|
| LIPID | PC | PE | SM | PS | PI[2] | PA[3] | Other |
| NATURAL[1] | 23.8 | 24.6 | 28.3 | 15.1 | 2.1 | 0.9 | 5.0 |
| ARTIFICIAL | 23.7 | 22.6 | 28.1 | 25.7 | n.a.[4] | n.a. | n.a. |

[1]Gordon, L.M. et al., supra
[2]PI = phosphatidylinositol
[3]PA = phosphatidic acid
[4]n.a. = not added Of every lipid stock solution, 500 µl were combined in a round-bottom flask and 1000, µl of the sodium cholate stock solution were added. The organic solvent was removed under a stream of nitrogen.

The lipid/detergent film was dispersed in 5.0 ml 10 mM PBS and sonicated for 10 minutes in a bath sonicator (Lab Supplies, Hicksville, N.Y.) until solubilization of the lipids was completed. The clear liquid was transferred to a teflon dialysis cell equipped with a Spectra/Por 2 membrane (MW cut-off 12–14,000) and dialyzed against 2 liters of PBS with 5 buffer changes after 4, 8, 16, 24, and 48 hours. The buffer was purged with $N_2$ over the entire time of dialysis. The samples were removed form the dialysis cell after a total dialysis time of 54–56 hours and stored at 4° C.

The size and size distribution of the artificial envelopes was analyzed using a NICOMP Model 370 laser particle sizer (Particle Sizing Systems, St. Barbara, Calif.). A typical example of a homogenous population of vesicles had an average size of 216 nm±82 nm (Std. Dev.) and a $chi^2$ value of 1.39. The reproducibility of preparation was remarkable. A total of 15 samples prepared was found to have an average diameter of 250 nm with an extremely narrow standard deviation of the mean of 26 nm.

The ultrastructure of the vesicles was determined by freeze-fracture electron microscopy. The results of the electron microscopy showed perfectly unilamellar artificial envelopes.

Cholesterol was determined according to the method of Zlatkis et al. (Zlatids, A., B. Zak, A. J. Boyle [1953] *J. Lab. Clin. Med.* 41:486–492). A total of 267.1 µg CH/ml, corresponding to 76.3% of the original total amount of CH, were recovered.

For phospholipid analysis a sample was extracted according to the method of Bligh and Dyer (Bligh, E. G., W. J. Dyer [1959] *Can. J. Biochem. Phys.* 37:911–917). A quantitative phospholipid assay was performed according to the method of Stewart (Stewart, J. C. M. [1980] *Anal. Biochem.* 104:10–14). In a typical experiment, a total of 613.8 µg PL/ml, corresponding to 74.0% of the original total amount of PL, was recovered.

The final phospholipid:cholesterol ratio was 0.87, only slightly different than the original ratio of 0.92.

EXAMPLE 2

Stability of Artificial HIV Envelopes (Without Protein)

Artificial HIV-1 envelopes (without protein) were stored at 4° C. in the refrigerator. Average size and size distribution were analyzed periodically by laser light scattering. Surprisingly, it was found that these envelopes were extremely stable with respect to retention of their original size. Examples of the size retention of four different batches stored over 20, 30, 60, 69, and 163 days, respectively, are shown in Table 4. Such practically ideal physical stability was a completely unexpected finding, since it is known that conventional liposomes of a comparable size and high cholesterol content "grow" upon storage due to the high free energy content of the highly curved membranes.

TABLE 4

Physical Stability of Artificial HIV-1 Envelopes

| Time from Prep | Average Size (nm) ± Size Distribution | | | |
|---|---|---|---|---|
| (Days) | Sample 1 | Sample 2 | Sample 3 | Sample 4 |
| 0 | 267 ± 137 | 216 ± 82 | 274 ± 106 | 234 ± 99 |
| 2 | 264 ± 123 | | | |
| 4 | | 211 ± 77 | | |
| 6 | 253 ± 111 | | | |
| 7 | | 208 ± 87 | | |
| 8 | 239 ± 92 | | | |

TABLE 4-continued

Physical Stability of Artificial HIV-1 Envelopes

| Time from Prep | Average Size (nm) ± Size Distribution | | | |
|---|---|---|---|---|
| (Days) | Sample 1 | Sample 2 | Sample 3 | Sample 4 |
| 15 | | 209 ± 89 | | |
| 15 | | 181 ± 48[1] | | |
| 17 | 252 ± 95 | | | |
| 20 | | 190 ± 57[1] | 247 ± 94 | |
| 30 | | 195 ± 58[1] | | |
| 60 | | | | 283 ± 112 |
| 69 | 285 ± 42 | | | |
| 163 | | | | 286 ± 91 |

[1]After the first reading on day 15, this sample was filtered through a 0.22 µm Acrodisc (Gelman) filter.

EXAMPLE 3

Preparation of Artificial HIV-1 Envelopes with gp160

Complete artificial HIV-1 envelopes containing the HIV-1 gp160 were prepared by a novel double-detergent dialysis technique. Double-detergent dialysis is a requirement because the high concentration of cholesterol in the lipid envelope requires a high concentration of detergent. Therefore, the dialysis is performed in two steps. The first step of preparing the lipid envelopes without the protein was essentially identical to the procedure described in Example 1, above. The second dialysis step consisted of the following procedure: The preformed envelopes were filtered through 0.22 µm filters (Acrodisc) and 2.5 ml of these were mixed under aseptic conditions with 0.5 ml of a filtered aqueous solution of deoxycholate (lipid:detergent molar ratio≈8) and incubated at room temperature for 1 hour. Partial solubilization was observed with electron microscopy of a vesicle sample treated similarly. gp160 (100 µg) was added aseptically, gently mixed, and kept for 45 minutes at room temperature. The mixture was then dialyzed in the cold (4° C.) against 2 liters of Tris (10 mM, pH 7.8, containing 0.5 mM $NaN_3$) with 5 buffer changes at 4, 8, 16, and 48 hours. The buffer was purged with $N_2$ for the entire time of dialysis. The sample was removed after 56 hours and analyzed for size and inclusion of gp160 on the outer vesicle surface by immunolabeling followed by electron microscopy (see Example 4).

EXAMPLE 4

Immunolabeling and Determination of gp1160 on the Surface of Artificial Envelopes Formvar coated nickel grids were treated with a 1% solution of poly-L-lysine for 10 minutes, briefly washed in water, and placed on a drop of the artificial envelopes. Envelopes were allowed to adsorb to the surface of the grid for one minute. Grids were floated on PBS for 10 minutes, followed by 10 minutes on 1% bovine serum albumin (BSA). After removal of excess BSA, the grids were incubated for 1 hour on a 1:250 dilution of the monoclonal antibody specific to gp160 (Cellular Products, Inc., Buffalo, N.Y.) or on an irrelevant monoclonal antibody. Grids were washed three times for 10 minutes each on PBS and incubated on a 1:20 dilution of goat anti-mouse IgG coupled to 15 nm colloidal gold for 1 hour. Grids were washed twice for 10 minutes in each PBS and distilled water. Grids were negatively stained with 1% uranyl acetate in water for 20 seconds, drained, and allowed to dry. The grids were observed on a Hitachi H-7000 electron microscope at 70 kV. Control lipid envelopes without protein were treated in an identical manner.

Monoclonal anti-gp160 antibody was found bound specifically to viral envelopes as visualized with the anti-mouse IgG-coupled gold, whereas viral envelopes treated with unrelated monoclonal antibody and lipid envelopes without protein treated with anti-gp160 antibody and the gold stain did not show gold-antibody binding.

EXAMPLE 5

Selective Binding of Artificial Envelopes to $CD4^+$ Cells

L. W. cells were derived at the University of Florida from the peripheral blood of a patient with HTLV-1 positive adult T-cell acute lymphoblastic leukemia. Flow cytometry analysis demonstrated these cells as 90–100% positive for the CD4 surface 5 antigen. The HL-60 cell line was obtained from ATCC, Rockville, Md. These cells are grown in suspension culture and have myeloblast/promyelocyte morphology. They lack specific markers for lymphoid cells. Approximately $1 \times 10^6$ cells in 0.5 ml were centrifuged at 1,000 ×g for 10 minutes; 10 µl of [$^{125}$I]-labeled envelopes, corresponding to $\approx 1 \times 10^6$ cpm (TCA-precipitate$\approx$54% of total counts), were added, and incubated on ice for 1 hour; 0.6 ml PBS were added; the sample was centrifuged, the pellet washed 5 times with PBS and bound 125I (cpm) counted in a gamma counter.

As shown in Table 5, counts associated with the $CD4^+$ L. W. cells were significantly higher than counts bound to $CD4^-$ control cells. This confirms the presence and conformational integrity of the gp160 on the artificial membrane surface and its affinity to the CD4 receptor.

TABLE 5

Selective binding of artificial envelopes to $CD4^+$ cells

| Cell Type | CD4 | [$^{125}$I] Binding (cpm) Avg. ± Std. (N = 3) |
|---|---|---|
| L.W. | + | 134,994 ± 20,529 |
| HL-60 | − | 82,614 ± 13,155 |

EXAMPLE 6

Preparation of Artificial RSV Envelopes with G and F Glycoproteins

Artificial RSV envelopes were prepared essentially identical to the method described in Example 1 and Example 3. Glycoprotein stock solutions contained 175 µg/ml G glycoprotein (MW$\approx$90,000) and 350 µg/ml F glycoprotein (MW$\approx$48,000), respectively.

Four samples of 1 ml lipid stock solution corresponding to 1.21 mg or 20.6 µmole total lipid were removed and dried under a stream of $N_2$ prior to redispersion and solubilization with sodium cholate followed by dialysis (Example 1). Since these samples were used to demonstrate fusogenicity of the artificial RSV envelopes, the fluorescent dye 6-carboxyfluorescein (6-CF) was added as aqueous space marker. A sample of nonspecific artificial envelopes without glycoprotein was used as control in fusion experiments (Example 7). In step 2, one sample was prepared with 46.3 µl of the G glycoprotein stock solution only, one sample with 8.2 µl of the F glycoprotein stock solution only, and one sample with both 46.3 µl of the G glycoprotein and 8.2 µl of the F glycoprotein stock solution. Deoxycholate was added and the samples processed as described in Example 3. The corresponding lipid:protein ratios are shown in Table 6. Prior to use in fusion tests (see Example 7) the artificial RSV envelopes were centrifuged for 10 minutes in an Eppendorff microfuge and the CF solution replaced with PBS.

TABLE 6

Lipid:Protein Ratio of Artificial RSV Envelopes

| Glycoprotein | Lipid Conc. (µmole/ml) | Glycoprotein Conc. (µmole/ml) | Molar Ratio |
|---|---|---|---|
| G | 20.6 | $9 \times 10^{-5}$ | $2.3 \times 10^5$ |
| F | 20.6 | $6 \times 10^{-5}$ | $3.4 \times 10^5$ |
| G + F | 20.6 | $1.5 \times 10^{-4}$ | $1.4 \times 10^5$ |

EXAMPLE 7

Fusion of Artificial RSV Viral Envelopes With HEp-2 Cells

HEp-2 cells were grown on sterile coverslip flasks at 37° C. and 5% $CO_2$. When the cells were approximately 50% confluent, they were washed with PBS and then used to perform fusion experiments as follows: To HEp-2 cells in Petri dishes were added 0.5 ml of one of the solutions containing the artificial envelopes without protein, with G glycoprotein only, with F glycoprotein only, or with both G and F glycoprotein as described in Example 5. An additional control was a solution containing 6-CF diluted 1:20,000 only (no lipid control). Cells were replenished with 3 ml of a 1% DMEM cell culture medium and incubated at 37° C. in 5% $CO_2$. Cells were viewed after 1, 2, 4, and 24 hours under a fluorescent microscope at 40X magnification and photographed under phase and fluorescent light.

Cells incubated with diluted CF solution did not fluoresce. Cells incubated with artificial RSV envelopes without protein showed only faint occasional fluorescence. There was no detectable fluorescence from a field of cells incubated with lipid envelopes without protein (lipid control). Also, cells incubated with artificial RSV envelopes containing G glycoprotein or F glycoprotein only showed some, but relatively faint, fluorescence. However, practically all cells of a batch that had been incubated with the complete artificial RSV envelopes were fluorescent after 1 hour incubation. Fluorescence is in all cases diffuse within the cytoplasm of the cells, which confirms that the transfer process was a fusogenic process rather than a phagocytic process which would result in punctate fluorescence confined to intracellular vacuoles. These results demonstrate that the complete artificial RSV envelope is highly fusogenic and may therefore be used as a drug carrier to deliver drugs directly into the cytoplasm of infected cells.

EXAMPLE 8

Asymetric Distribution of Lipids

For certain biological membranes, lipids are distributed asymmetrically within the membrane. One example for this is the red blood cell membrane. However, this has never been demonstrated or reported for artificial lipid membranes. Tests were conducted to determine the membrane distribution of lipids for vesicles made according to the methods of the subject invention. Specifically, the distribution of phosphatidylethanolamine (PE) and phosphatidylserine (PS) in the artificial viral envelope membranes was determined using a fluorescent marker (fluorescamine; FC) which binds selectively to these two lipids using the following procedure. 0.2 ml of the artificial viral envelope dispersion was diluted with 4 ml phosphate buffered saline (PBS) and a small amount of FC was added. Following shaking for 30 minutes in order to achieve equilibrium of binding of FC to the outer surface of the viral membranes the solution was centrifuged at 3.000 rpm for 15 minutes to remove potential aggregates. Fluorescence in the supernatant was measured. With the excitation wavelength set to 370 nm. fluorescence intensities were recorded at 460 and 520 nm. corresponding to the fraction of FC bound to the outer surface of the artificial viral envelope membranes. In order to determine the total amount of PE and PS in the membranes (inside and outside). the membranes were solubilized by adding 4 μl of Triton-X-100 (10% w/v aqueous solution). FC was added and the resulting fluorescence intensities recorded as above.

The formula used to calculate the mole fractions of PE and PS in the artificial viral envelopes was:

$$F520^{exp}/F460^{exp} = F520^{PS}/F460^{PS} \times m_1 + F520^{PE}/F460^{PE} \times m_2$$

where $F520^{exp}$ and $F460^{exp}$ are the fluorescence intensities measured at 520 and 460 nm. respectively. $F520^{PS}$ and $F460^{PS}$, and $F520^{PE}$ and $F460^{PE}$ are the molar fluorescence intensities of PS and PE at both wavelengths. and $m_1$ and $m_2$ are the mole fractions of PS and PE. respectively.

Experimental results were as follows:

TABLE 7

Surface and total fluorescence intensities at 460 and 520 nm.

|  | F460 (avg.) | ± S.D. | F520 (avg.) | ± S.D. |
|---|---|---|---|---|
| surface[1] | 11.3 | 0.37 | 7.3 | 0.25 |
| total[1] | 70.13 | 3.47 | 47.7 | 2.3 |

[1]n = 3

TABLE 8

Total and surface mole fractions of PE and PS calculated

|  | $m_1$ (avg.) (PS) | ± S.D. | $m_2$ (avg.) (PE) | ± S.D. |
|---|---|---|---|---|
| surface[1] | 0.675 | 0.06 | 0.325 | 0.045 |
| total[1] | 0.264 | 0.02 | 0.736 | 0.025 |

[1]n = 3

TABLE 9

Percent of PE and PS at the viral envelope surface

| Lipid | Percent (%) | ± S.D. (n = 3) |
|---|---|---|
| PE | 7.1 | 1.5 |
| PS | 41.2 | 2.1 |

From these results it can be seen that. during the unique controlled preparation of artificial viral envelopes according to the subject invention. a specific arrangement of phospholipid occurs which is most likely due to an energetically favorable asymmetric assembly of the phospholipid head groups (PE. PS. PC. and SM head groups differ in size. as well as net charge). resulting in an asymmetric distribution with the majority of PE (92.9%) and PS (58.8%) being enriched on the inner membrane leaflet. This is a new and unexpected finding which. to our knowledge. has never been observed or reported before for any kind of artificial lipid membranes.

EXAMPLE 9

Selective Arrest of CD4+ MOLT4 Cell Growth by Artificial Viral Envelopes Exhibiting HIV-1 gp1160 and Having Encapsulated Ricin-A In order to test the ability of our viral envelopes to arrest CD4+ MOLT4 cell growth. we encapsulated ricin-A in our viral envelopes. which were prepared with gp160 at the surface. These toxin-containing viral envelopes were then added to the MOLT4 cells. For controls. we added ricin-A alone (not encapsulated) to the MOLT4 cells. we added ricin-A encapsulated in viral envelopes without gp160 at the surface. and we added viral envelopes having gp160 but no ricin-A. Only the gp160 viral envelopes with encapsulated ricin-A arrested the growth of the MOLT4 cells.

Ricin-A at a concentration of 2 ng/ml to 8 ng/ml was added to MOLT4 (CD4+) cells in culture and cell growth followed for 60 hours. Also. ricin-A at a concentration of 2 ng/ml encapsulated into artificial viral envelopes exhibiting recombinant gp160 was added to MOLT4 cells in culture and cell growth followed over 60 hours. Control experiments included empty viral envelopes and viral envelopes containing ricin-A without gp160 inserted in the membrane. The experiment with 2 ng/ml ricin-A in gp160-exhibiting artificial viral envelopes was also performed in the presence of 0.1 μg/ml anti-gp160 monoclonal antibody in the medium.

Artificial viral envelopes were prepared as in Example 1 and Example 3. respectively. MOLT4 cell growth was not inhibited and was essentially identical to the growth curve of untreated cells in the presence of 2–8 ng/ml free ricin-A. However. 2 ng/ml ricin-A incorporated in gp160 artificial viral envelopes completely arrested MOLT4 cell growth. Cell growth was normal again when the same experiment was performed in the presence of 0.1. μg/ml anti-gp160 monoclonal antibody. Control cell cultures incubated with artificial viral envelopes only (≈1 μg lipid/ml). or with 2 ng/ml ricin-A-containing artificial viral envelopes without gp160 present exhibited normal cell growth.

EXAMPLE 10

Selective Intracellular Delivery of a Marker Plasmid (pCAT) Encapsulated Within HIV-1 gp160-Exhibiting Artificial Viral Envelopes to CD4+ Cells (REX-1B and KG-1)

Artificial viral envelopes were prepared as in Example 1 and Example 3. respectively. pCAT (4.53 mg) was dissolved in 3 ml Tris. pH 8.0. and combined with 13.5 mg total lipid. CD4+ cells (REX-1B and KG-1) (2×10$^6$ cells/dish) were incubated with the artificial viral envelopes containing pCAT and exhibiting HIV-1 gp160 for 1 hour at room temperature. washed 3× with PBS. and resuspended. pCAT in solution served as control. After washing and resuspension. cells were incubated for 48 hours at 37° C. to allow expression of CAT. Acetylated $^{14}$C-chloramphenicol was assayed by a standard procedure. The activity of CAT 48 hours after transformation of REX-1B and KG-1 cells over a 60 minute incubation period with pCAT-carrying artificial viral envelopes was clearly superior to the expression of CAT when incubated with pCAT in solution.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A synthetic lipid vesicle comprising a membrane with an outer surface wherein said vesicle comprises cholesterol, phospholipid, and a protein inserted into said membrane, wherein said vesicle is prepared by a process comprising:
   (a) treating a preformed lipid vesicle having a cholesterol:phospholipid molar ratio of at least about 0.8:1 with an anionic detergent;
   (b) contacting the treated lipid vesicle with said protein; and
   (c) removing said detergent.

2. A synthetic lipid vesicle comprising a membrane with an outer surface wherein said vesicle comprises cholesterol, phospholipid, and a protein inserted into said membrane, wherein said vesicle is obtainable by a process comprising:
   (a) treating a preformed lipid vesicle having a cholesterol:phospholipid molar ratio of at least about 0.8:1 with an anionic detergent;
   (b) contacting the treated lipid vesicle with said protein; and
   (c) removing said detergent.

3. The synthetic lipid vesicle of claim 2, wherein said preformed lipid vesicle is formed in the absence of protein.

4. The synthetic lipid vesicle of claim 2, wherein said preformed lipid vesicle is formed by a process comprising solubilizing a mixture of cholesterol, phospholipid, and detergent, and then removing the detergent by dialysis.

5. The synthetic lipid vesicle of claim 2, wherein said preformed lipid vesicle treated in step (a) is provided in a preparation that is substantially free of detergent.

6. The synthetic lipid vesicle of claim 2, wherein the treating in step (a) is performed before said protein is added to said preformed lipid vesicle.

7. The synthetic lipid vesicle of claim 2, wherein the removing of the detergent in step (c) is performed by dialysis.

8. The synthetic lipid vesicle of claim 2, comprising a cholesterol:phospholipid molar ratio of between about 0.8:1 and about 1.2:1.

9. The synthetic lipid vesicle of claim 2, comprising phosphatidyl serine and phosphatidyl ethanolamine.

10. The synthetic lipid vesicle of claim 2, the phospholipid of which comprises at least about 18 mole percent of phosphatidyl serine, phosphatidyl inositol, phosphatidic acid, or a combination thereof.

11. The synthetic lipid vesicle of claim 2, which is between about 150 and about 500 nm in size.

12. The synthetic lipid vesicle of claim 2, wherein said protein is a recombinant protein.

13. The synthetic lipid vesicle of claim 2, wherein said protein is a purified protein.

14. The synthetic lipid vesicle of claim 2, wherein said protein comprises a protein or protein epitope from a virus.

15. The synthetic lipid vesicle of claim 14, wherein the viral protein or protein epitope is selected from the group consisting of HIV-1 gp160, RSV G protein, and RSV F protein.

16. The synthetic lipid vesicle of claim 2, wherein said protein is a fusion protein or a membrane perturbing agent.

17. The synthetic lipid vesicle of claim 2, wherein said protein has an embedded end and a free end, and wherein said free end comprises a cysteine residue.

18. The synthetic lipid vesicle of claim 17, comprising a toxin conjugated to said free end of said protein via a disulfide bond.

19. The synthetic lipid vesicle of claim 2, comprising encapsulated material selected from the group consisting of DNA, RNA, and oligodeoxynucleotides.

20. The synthetic lipid vesicle of claim 2, wherein said encapsulated material comprises a plasmid, a gene, an antisense construct, or a ribozyme.

21. The synthetic lipid vesicle of claim 2, wherein said protein is recognized by a cell surface receptor.

22. The synthetic lipid vesicle of claim 2, wherein said anionic detergent is a bile salt or bile acid.

23. The synthetic lipid vesicle of claim 2, wherein said vesicle is unilamellar.

24. A formulation for administration to a human or animal, comprising the synthetic lipid vesicle of claim 2 encapsulating a material selected from the group consisting of drugs, toxins, proteins peptides DNA, RNA, and oligodeoxynucleotides.

25. A synthetic vaccine, comprising an effective amount of the synthetic lipid vesicle of claim 14.

26. A method for biological delivery of a material, comprising the administration of the synthetic lipid vesicle of claim 2 encapsulating said material.

27. A method for transferring genetic material to human cells, comprising contacting the cells with the synthetic lipid vesicle of claim 19.

28. A method for treatment of a human or animal disease, comprising administration of the formulation according to claim 24.

* * * * *

UNITED STATES PATENT AND TRADEMARK OFFICE
CERTIFICATE OF CORRECTION

PATENT NO. : 5,766,625

DATED : June 16, 1998

INVENTOR(S) : Hans Schreier, Ramesh Chander, Arlene A. Stecenko

It is certified that error appears in the above-identified patent and that said Letters Patent is hereby corrected as shown below:

Column 1, line 45: "CR Acad." should read --C.R. Acad.--

Column 4, line 4: "45 1," should read --45:1,--

Column 6, line 3: "to. lymphocytes" should read --to lymphocytes--

Column 7, line 9: "(HTLV-VII" should read --(HTLV-I/II--

Column 7, line 13: "Senilild Forest" should read --Semliki Forest--

Column 7, line 20: "(CILs);" should read --(CTLs);--

Column 7, line 29: "imrnian" should read --simian--.

Column 7, line 32: "Corynebactenum" should read --Corynebacterium--

Column 7, line 33: "Neissefia" should read --Neisseria--

Column 7, line 37: "Vibiio" should rea --Vibrio--

Column 7, line 37: "bumetii" should read --burnetii--

UNITED STATES PATENT AND TRADEMARK OFFICE
CERTIFICATE OF CORRECTION

Page 2 of 3

PATENT NO. : 5,766,625

DATED : June 16, 1998

INVENTOR(S) : Hans Schreier, Ramesh Chander, Arlene A. Stecenko

It is certified that error appears in the above-identified patent and that said Letters Patent is hereby corrected as shown below:

Column 7, line 41: "Eimefia" should read --Eimeria--

Column 7, line 58: "thuningiensis" should read --thuringiensis--

Column 7, line 64: "Rno Viral" should read --RNA. Viral--

Column 7, line 67: "ilarvirusec," should read --ilarviruses,--

Column 8, line 52: "HIodgkin's" should read --Hodgkin's--

Column 9, line 32: "KCI" should read --KCl--

Column 9, line 38: "100 µ/ml" should read --100 µg/ml--

Column 11, line 22: "(Zlatids," should read --(Zlatkis,--

Column 12, line 51: "gpl160" should read --gp160--

Column 13, line 20: "CD4 surface 5 antigen" should read --CD4 surface antigen--

Column 15, line 66: "in size. as" should read --in size as--

UNITED STATES PATENT AND TRADEMARK OFFICE
CERTIFICATE OF CORRECTION

PATENT NO. : 5,766,625

DATED : June 16, 1998

INVENTOR(S) : Hans Schreier, Ramesh Chander, Arlene A. Stecenko

It is certified that error appears in the above-identified patent and that said Letters Patent is hereby corrected as shown below:

Column 16, line 9: "gpl160" should read --gp160--

Column 16, line 41: "0.1, µg/ml" should read --0.1 µg/ml--

Column 18, line 38: "drugs, toxins, proteins peptides DNA, RNA, and" should read --drugs, toxins, proteins, peptides, DNA, RNA, and--

Signed and Sealed this

Fifth Day of January, 1999

*Attest:*

*Attesting Officer*    *Acting Commissioner of Patents and Trademarks*